United States Patent
van Zon et al.

(10) Patent No.: US 11,694,809 B2
(45) Date of Patent: Jul. 4, 2023

(54) PATIENT MONITORING SYSTEMS AND METHODS

(71) Applicant: KONINKLIJKE PHILIPS N.V., Eindhoven (NL)

(72) Inventors: Cornelis Conradus Adrianus Maria van Zon, Cambridge, MA (US); William Palmer Lord, Fishkill, NY (US); Abigail Flower, Mahopac, NY (US)

(73) Assignee: Koninklijke Philips N.V., Eindhoven (NL)

( * ) Notice: Subject to any disclaimer, the term of this patent is extended or adjusted under 35 U.S.C. 154(b) by 115 days.

(21) Appl. No.: 16/339,055

(22) PCT Filed: Sep. 28, 2017

(86) PCT No.: PCT/EP2017/074588
§ 371 (c)(1),
(2) Date: Apr. 3, 2019

(87) PCT Pub. No.: WO2018/065284
PCT Pub. Date: Apr. 12, 2018

(65) Prior Publication Data
US 2019/0287682 A1 Sep. 19, 2019

Related U.S. Application Data

(60) Provisional application No. 62/404,294, filed on Oct. 5, 2016.

(51) Int. Cl.
*G16H 50/30* (2018.01)
*G16H 40/20* (2018.01)
(Continued)

(52) U.S. Cl.
CPC .......... *G16H 50/30* (2018.01); *A61B 5/0002* (2013.01); *G16H 40/20* (2018.01); *G16H 50/80* (2018.01); *G16H 50/20* (2018.01); *G16H 80/00* (2018.01)

(58) Field of Classification Search
CPC ...... A61B 5/0002; G16H 40/20; G16H 50/20; G16H 50/30; G16H 50/80; G16H 80/00
(Continued)

(56) References Cited

U.S. PATENT DOCUMENTS 6,786,406 B1   9/2004  Maningas
9,208,288 B2  12/2015  Putrino
(Continued)

FOREIGN PATENT DOCUMENTS

WO   2004110267 A2  12/2004
WO  20150236502 A1   9/2015

*Primary Examiner* — Michael Tomaszewski

(57) ABSTRACT

Techniques disclosed herein relate to monitoring changes in conditions of multiple individuals in areas. In some embodiments, a patient monitoring queue may be established (504) that includes a plurality of patients in an area (104, 304) such as a waiting room. The area may be capturable by vital sign acquisition camera(s) (276. 376, 476) mounted in or near the area. Updated vital sign(s) may be unobtrusively acquired (510) by the vital sign acquisition camera(s) from a given patient selected (506) from the patient monitoring queue. Based on the updated vital sign(s) and prior vital signs acquired previously from the given patient, deterioration of the given patient may be detected (512). Output may be provided (514) alerting medical personnel of the deterioration of the given patient.

15 Claims, 7 Drawing Sheets

(51) Int. Cl.
  *A61B 5/00* (2006.01)
  *G16H 50/80* (2018.01)
  *G16H 50/20* (2018.01)
  *G16H 80/00* (2018.01)

(58) Field of Classification Search
  USPC .................................................... 705/2–3
  See application file for complete search history.

(56) References Cited

U.S. PATENT DOCUMENTS

| | | | |
|---|---|---|---|
| 10,095,833 B2 | 10/2018 | Balram | |
| 10,504,616 B2 | 12/2019 | Kawai et al. | |
| 2003/0125610 A1 | 7/2003 | Sachs et al. | |
| 2004/0254472 A1* | 12/2004 | McQuilkin | A61B 5/015 600/473 |
| 2007/0040889 A1 | 2/2007 | Sahashi | |
| 2008/0001735 A1* | 1/2008 | Tran | G06F 19/00 340/539.22 |
| 2008/0249801 A1* | 10/2008 | Zaleski | G16H 40/67 705/2 |
| 2008/0294018 A1* | 11/2008 | Kurtz | G16H 10/60 600/301 |
| 2010/0256462 A1* | 10/2010 | Rappaport | A61B 5/00 600/301 |
| 2014/0194793 A1* | 7/2014 | Nakata | A61N 1/36031 601/48 |
| 2014/0303454 A1 | 10/2014 | Clifton et al. | |
| 2015/0310183 A1* | 10/2015 | Madhavan | G16H 40/67 705/3 |
| 2016/0019352 A1* | 1/2016 | Cohen | G16H 10/60 705/3 |
| 2016/0029890 A1* | 2/2016 | Stump | A61B 5/0022 600/301 |
| 2016/0029980 A1 | 2/2016 | Osherov | |
| 2016/0188831 A1* | 6/2016 | Kurtz | G16H 10/60 705/2 |
| 2017/0262604 A1* | 9/2017 | Francois | G16H 70/60 |
| 2017/0323064 A1* | 11/2017 | Bates | G16H 50/20 |
| 2019/0298270 A1* | 10/2019 | Al-Ali | A61B 5/684 |

\* cited by examiner

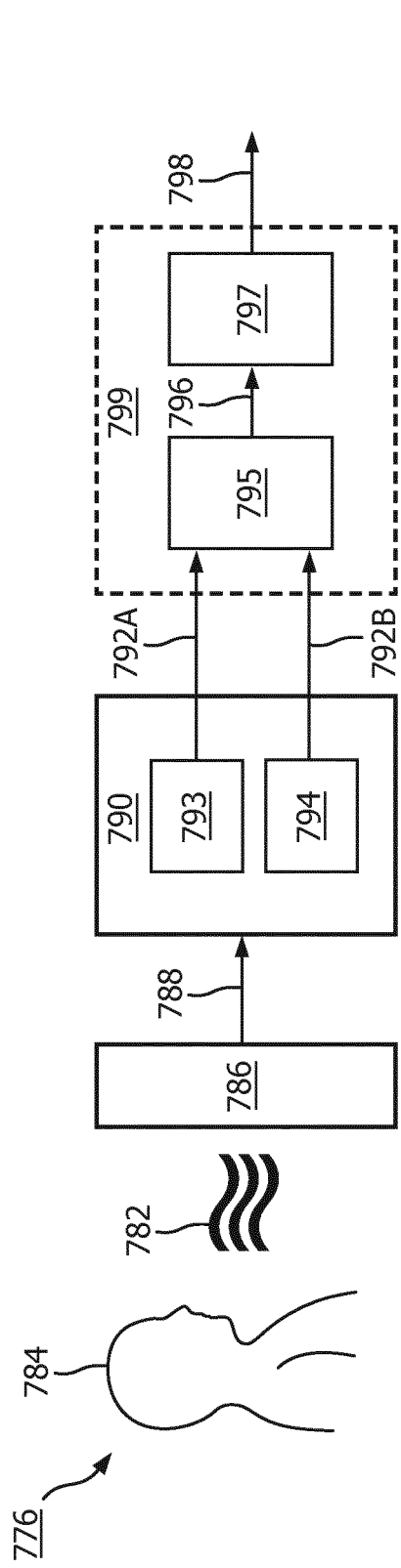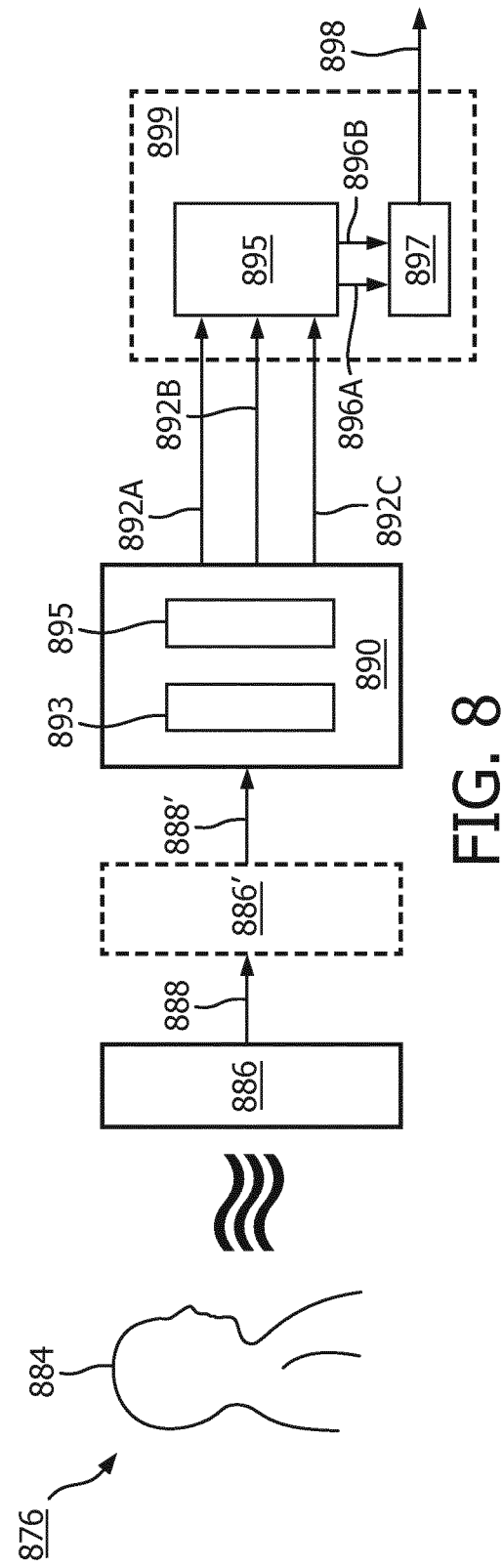

PATIENT MONITORING SYSTEMS AND METHODS

CROSS-REFERENCE TO PRIOR APPLICATIONS

This application is the U.S. National Phase application under 35 U.S.C. § 371 of International Application No. PCT/EP2017/074588, filed on Sep. 28, 2017, which claims the benefit of Provisional Application Ser. No. 62/404,94, filed Oct. 5, 2016. These applications are hereby incorporated by reference herein, for all purposes.

TECHNICAL FIELD

The present disclosure is directed generally to health care. More particularly, but not exclusively, various methods and apparatus disclosed herein relate to monitoring changes in conditions of multiple individuals such as patients in areas such as waiting rooms.

BACKGROUND

When patients visit the hospital, they typically are triaged to determine various information about the patients, such as their names, ages, heights, weights, vital signs, reasons for visiting, and other similar information. Once triaged, the patients are sent to an area such as a waiting room to wait for hospital resources such as physicians to become available to examine and/or treat the patients. Wait times for the patients may be significant depending on availability of hospital resources. It is not uncommon for patients to deteriorate while waiting, and medical personnel may not always become aware of the deterioration in a timely fashion.

SUMMARY

The present disclosure is directed to methods, systems, and apparatus for monitoring changes in conditions of multiple individuals such as patients in an area such as waiting rooms. For example, a plurality of triaged patients may wait in a waiting room until they can be seen by an emergency room ("ER") physician. The patients may be included in a patient monitoring queue (also referred to simply as a "patient queue") that is ordered or ranked, for instance, based on a measure of acuity associated with each patient (referred to herein as a "patient acuity measure") that is determined based on information obtained/acquired from the patient by a triage nurse, as well as other data points such as patient waiting time, patient presence, etc. One or more "vital sign acquisition cameras" mounted in the waiting room may be configured to periodically perform contactless and/or unobtrusive acquisition of one more updated vital signs and/or physiological parameters from each patient. These updated vital signs and/or physiological parameters may include but are not limited to temperature, pulse, oxygen saturation ("$SO_2$"), respiration rate, skin color, posture, sweat levels, and so forth. In some embodiments, if the updated vital signs and/or a difference between updated and previously-acquired vital signs and/or physiological parameters (e.g., initial vital signs obtained at triage, previous updated vital signs acquired by the vital sign acquisition cameras) satisfy one or more thresholds, an alert may be raised to notify medical personnel of deterioration of the patient. The medical personnel may then take immediate action.

Generally, in one aspect, a method may include: establishing, by one or more processors, a patient monitoring queue that includes a plurality of patients in an area, wherein the area can be captured by one or more vital sign acquisition cameras; unobtrusively acquiring, by one or more of the vital sign acquisition cameras, one or more updated vital signs from a given patient selected from the patient monitoring queue; detecting, by one or more of the processors, based on the one or more updated vital signs and prior vital signs acquired previously from the given patient, deterioration of the given patient; and providing, by one or more of the processors, output alerting medical personnel of the deterioration of the given patient.

In various embodiments, the method may further include receiving, by one or more of the processors, a patient acuity measure associated with each patient of the plurality of patients in the area, wherein the patient acuity measure associated with each patient is based on one or more initial vital signs acquired from the patient, and wherein the patient monitoring queue is ranked based at least in part on the patient acuity measures. In various embodiments, the one or more initial vital signs acquired from each patient may be acquired with medical equipment that is different than the one or more vital sign acquisition cameras.

In various embodiments, the given patient may be selected from the patient monitoring queue based on a position of the given patient in the patient monitoring queue. In various embodiments, the method may further include altering, by one or more of the processors, a position of the given patient in the patient monitoring queue based at least in part on an updated patient acuity measure determined in response to the output alerting medical personnel of the deterioration of the patient.

In various embodiments, the output may include at least one of the given patient's name, gender, most recent vital signs, vital sign trend, a reference image of the given patient, or a location of the given patient in the area. In various embodiments, the method may further include identifying, by one or more of the processors, the given patient among the plurality of patients in the area based on a reference image depicting the given patient. In various embodiments, the reference image may be captured by one or more of the vital sign acquisition cameras. In various embodiments, the reference image may be captured by one or more cameras associated with a triage station or registration desk associated with the medical waiting room. In various embodiments, the one or more vital sign acquisition cameras includes a pan-tilt-zoom ("PTZ") camera.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the disclosure.

FIGS. 7 and 8 schematically depict example components of vital sign acquisition cameras, in accordance with various embodiments.

DETAILED DESCRIPTION

When patients visit the hospital, they typically are triaged to determine various information about the patients, such as their names, ages, heights, weights, vital signs, reasons for visiting, and other similar information. Once triaged, the patients are sent to an area such as a waiting room to wait for hospital resources such as physicians to become available to examine and/or treat the patients. Wait times for the patients may be significant depending on availability of hospital resources. It is not uncommon for patients to deteriorate while waiting, and medical personnel may not always become aware of the deterioration in a timely fashion. Accordingly, techniques described herein facilitate automatic and unobtrusive (e.g., contactless) monitoring of patients' conditions in an area such as a waiting room, so that alerts may be provided to medical personnel when a deterioration of a patient warrants immediate medical attention.

The following are definitions of terms as used in the various embodiments of the present invention. The term "database" as used herein refers to a collection of data and information organized in such a way as to allow the data and information to be stored, searched, retrieved, updated, and manipulated and to allow them to be presented into one or more formats such as in table form or to be grouped into text, numbers, images, and audio data. The term "database" as used herein may also refer to a portion of a larger database, which in this case forms a type of database within a database. "Database" as used herein also refers to conventional databases that may reside locally or that may be accessed from a remote location, e.g., remote network servers. The database typically resides in computer memory that includes various types of volatile and non-volatile computer storage. Memory wherein the database resides may include high-speed random access memory or non-volatile memory such as magnetic disk storage devices, optical storage devices, and flash memory. Memory where the database resides may also comprise one or more software for processing and organizing data received by and stored into the database.

Figure 1:
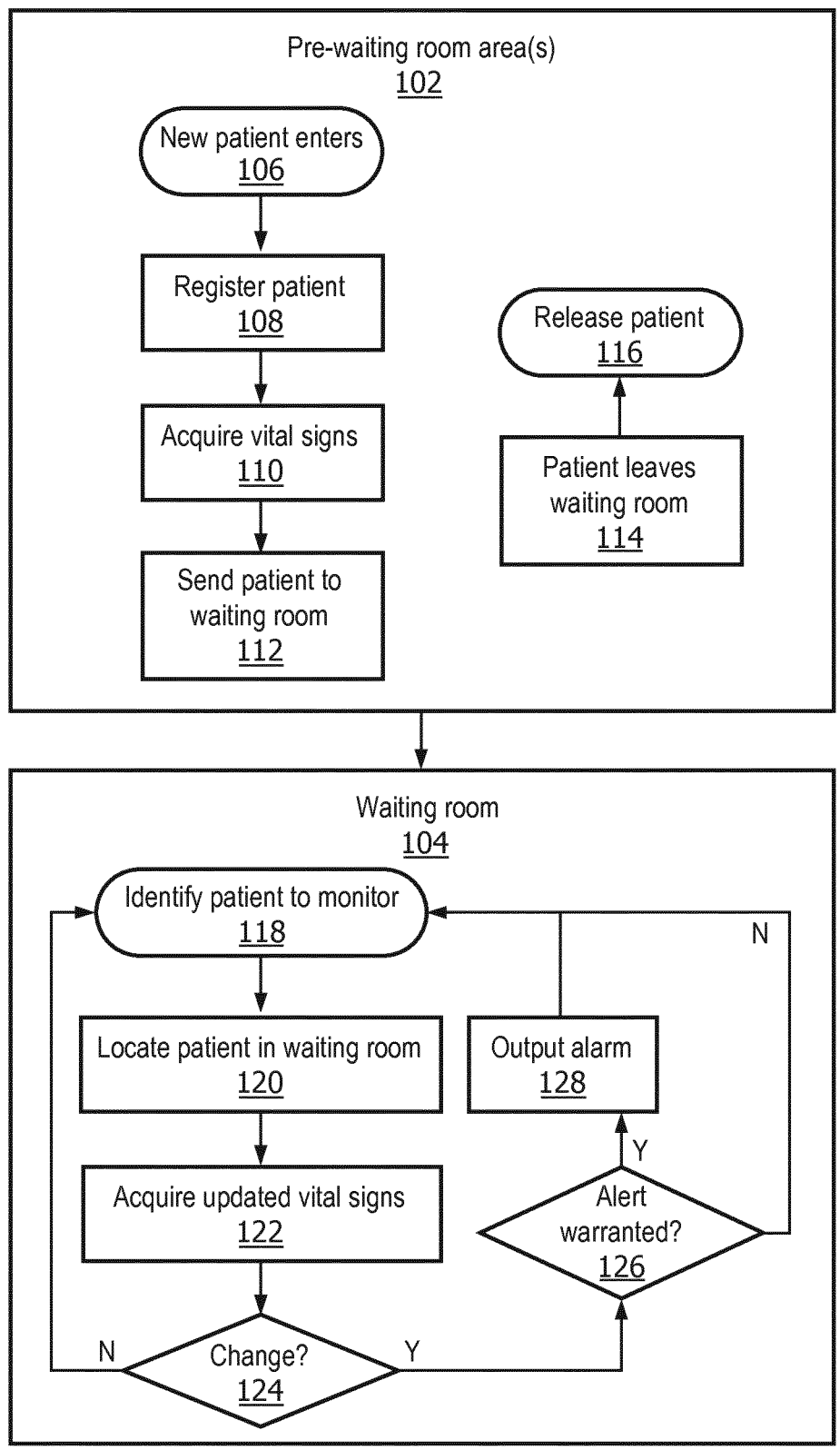
FIG. 1 schematically illustrates a general process flow for patients monitored using disclosed techniques, in accordance with various embodiments.

FIG. 1 schematically illustrates generally how patients may be monitored using disclosed techniques. In particular, operations and actions are depicted that may occur in a pre-waiting room area, such as at a pre-waiting room area(s) 102, which may include reception and/or registration, and/or a triage station or booth. In addition, operations and actions are depicted that may occur in a waiting room 104. At block 106, a new patient may enter and/or approach pre-waiting room area(s) 102, e.g., after checking in at a reception desk (not depicted).

At block 108, the new patient may be registered. Registration may include, for instance, collecting information about the patient such as the patient's name, age, gender, insurance information, and reason for visit. Typically, but not exclusively, this information may be manually input into a computer by medical personnel such as a triage nurse. In some embodiments, one or more reference images of the patient may be acquired, e.g., by a camera that is integral with a computing device operated by the triage nurse, by a standalone camera, and/or by a vital sign acquisition camera (in which case at least some vital signs may be optionally acquired at registration). In many instances, the triage nurse additionally may acquire various initial vital signs and/or physiological parameters at block 110 using various medical instruments. These initial vital signs and/or physiological parameters may include but are not limited to blood pressure, pulse, glucose level, $SO_2$, photoplethysmogram ("PPG"), respiration rate (e.g., breathing rate), temperature, skin color, and so forth. While not depicted in FIG. 1, in some embodiments, other information may be gathered at triage as well, such as acquiring/updating a patient's medical history, determining patient allergies, determining patient's use of medications, and so forth.

Once the patient is registered and their initial vital signs and/or physiological parameters acquired, at block 112, the patient may be sent to waiting room 104. In some embodiments, the patient may be assigned a so-called "patient acuity measure," which may be a measure that is used to rank a severity of the patient's ailment, and in some instances may indicate an anticipated need for emergency room resources. Any number of commonly used indicators and/or clinician decision support ("CDS") algorithms may be used to determine and/or assign a patient acuity measure, including but not limited to the Emergency Severity Index ("ESI"), the Taiwan Triage System ("TTS"), the Canadian Triage and Acuity Scale ("CTAS"), and so forth. For example, in some embodiments, vital signs of the patient may be compared with predefined vital sign thresholds stored in a system database, or with published or known vital sign values typical for a given patient age, gender, weight, etc., to determine the patient's initial patient acuity measure and/or the patient's initial position in the patient queue. In some embodiments, various physiological and other information about the patient may be fed into a trained model (e.g., regression model, neural network, deep learning network, etc.), case-based reasoning algorithm, or other clinical reasoning algorithm to derive one or more acuity measures. In some embodiments, the information used for deriving the acuity measure may include or even be wholly limited to vitals or other information that may be captured by the vital sign acquisition camera. In some embodiments, the information used for deriving the acuity measure may alternatively or additionally include information such as information from a previous electronic medical record (EMR) of the patient, information acquired from the patient at triage, information from wearable devices or other sensors carried by the patient, information about other patients or people in the waiting room (e.g., vitals of others in the room), information about family members or others associated with the patient (e.g., family member EMRs), etc.

At block 114, it may be determined, e.g., using one or more cameras, sensors, or input from medical personnel, that a patient has left the waiting room. Block 114 may include scanning each person currently within the waiting room (e.g., as part of a seeking function that attempts to locate the patient once the patient is at top of a queue of patients for which vitals are to be captured, such as an execution of block 120 described below, or cycling through each person in the room to capture vitals, as multiple executions of the loop including blocks 118 and 120 described below) and determining that the patient was not located. In some embodiments, the system may wait until a predetermined number of instances of the patient missing is reached or a predetermined amount of time has passed during which the patient is missing before the patient is deemed to have left the waiting room to account for temporary absences (e.g., visiting the restroom or speaking with clinical staff in a triage room). For example, the patient may have been taken into the ER proper because it is their turn to see a doctor. Or the patient's condition may have improved while they waited, causing them to leave the hospital. Or the patient may have become impatient and left to seek care elsewhere. Whatever the reason, once it is determined that the patient has left the waiting room for at least a threshold amount of time, at block 116, the patient may be released from the system, e.g., by removing them from a queue in which registered patients are entered.

At block 118, a patient in waiting room 104 may be identified for monitoring using techniques described herein. For example, in some embodiments, a database storing registration information obtained at blocks 108-110 may be searched to identify a patient having the highest patient acuity measure or a patient having the highest acuity measured that has not been monitored recently, as may be determined by a time threshold set for all patients or set (e.g., inversely correlated) based on the acuity measure). In other embodiments, registration information associated with a plurality of patients in waiting room may be ranked in a patient monitoring queue, e.g., by their respective patient acuity measures, in addition to or instead of other measures such as waiting times, patient presence in the waiting room (e.g., missing patients may be selected for monitoring more frequently to determine whether they should be released if repeatedly absent), etc. In yet other embodiments, patient acuity measures may not be considered when ranking the patient monitoring queue, and instead only considerations of patient waiting times, patient presence, etc., may be considered.

However such a patient monitoring queue is ranked, in some embodiments, the first patient in the queue may be identified as the one to be monitored next. It is not required (though it is possible) that the patient monitoring queue be stored in sequence of physical memory locations ordered by patient acuity measures. Rather, in some embodiments, a ranked patient monitoring queue may merely include a rank or priority level value associated with each patient. In other words, a "patient monitoring queue" as described herein may refer to a "logical" queue that is logically ranked based on patient acuity measures, waiting time etc., not necessarily a contiguous sequence of memory locations. Patients may be identified for monitoring at block 118 in an order of their respective ranking in the patient monitoring queue.

At block 120, the patient identified at block 118 may be located in waiting room 104. In various embodiments, one or more vital sign acquisition cameras (not depicted in FIG. 1, see FIGS. 2, 7 and 8) deployed in or near waiting room 104 may be operated to scan various visual features of patients in waiting room 104 to match those features to a reference patient image captured during registration at block 108. Visual features of patients that may be matched to corresponding features of patient images include but are not limited to faces, hair, clothing, torsos, and so forth.

In other embodiments, no patient monitoring queue may be established. Instead, vital sign acquisition cameras may simple be configured to pan, tilt, and/or zoom so that their respective fields of view move across predetermined trajectories of waiting room 304. For example, vital sign acquisition cameras may be configured to sequentially scan across rows of chairs, and/or to sequentially scan through areas of waiting room 104 known to be commonly inhabited by patients. In such embodiments, as each face is captured, it is matched against patient records to identify the patient to which the face corresponds so that vitals may be captured and correlated to the correct patient or person.

In various embodiments, the system may not be limited to only monitor patients that have been registered in the system (e.g., according to steps 108-112). For example, it is possible that a companion of a patient in the waiting room may develop a condition that requires attention, even though they themselves were not registered as a patient. As another example, a patient may not go through registration 108-112 and simply sit down in the waiting room because the waiting room/registration stations are busy, they do not know to register, they choose not to register, etc. In such embodiments, the system may detect a non-registered person by capturing an image/video of their face (or capture other identifying features) and fail to find a matching patient record among the registered patients. In such a case, the system may create a new record to represent the unknown patient, capture vitals for storage in the record as initial vitals measurements, and record the image/video as a reference image (or attempt to capture one or more additional images/videos, potentially from better angles, for subsequent use as reference images). If an alert or other information about the unknown patient is to be displayed to the waiting room staff (e.g., as described below), the information may be displayed along with one or more of these reference images/videos to aid the staff in identifying the person in the waiting room to which the alert or other information corresponds. If the person is later registered according to steps 108-112, the new information may be merged into the "unknown person" record either manually (e.g., by staff manually selecting the existing record which is to be supplemented with registration information) or automatically (e.g., by later comparing the reference images of the two records and determining they correspond to the same person, or by later encountering difficulty/ambiguity by matching the person to both records during a vitals capture sequence).

At block 122, one or more vital sign acquisition cameras mounted or otherwise deployed in or near waiting room 104 may be operated to perform unobtrusive (e.g., contactless) acquisition of one or more updated vital signs and/or physiological parameters from the patient identified at block 118 and located at block 120. These vital sign acquisition cameras may be configured to acquire (without physically contacting the patient) a variety of different vital signs and/or physiological parameters from the patient, including but not limited to blood pressure, pulse (or heart rate), skin color, respiratory rate, PPG, $SO_2$, temperature, posture, sweat levels, and so forth.

In some embodiments, vital sign acquisition cameras may be equipped to perform so-called "contactless methods" to acquire vital signs and/or extract physiological information from a patient may be used as medical image devices. Non-limiting examples of such cameras are described in United States Patent Application Publication Nos. 20140192177A1, 20140139656A1, 20140148663A1, 20140253709A1, 20140235976A1, and 20140275880A1, which are incorporated herein by reference for all purposes. FIGS. 7 and 8 schematically depict two non-limiting configurations of vital sign acquisition cameras that may be employed in various embodiments of the present disclosure.

In some embodiments, one technique for determining a patient's heart rate or pulse may be to monitor the patient's facial skin color. Micro-changes in skin color that are caused by blood flow may be detected by a vital sign acquisition camera. These detected micro-changes may be used to determine a pulse rate of the patient. Facial skin color changes due to varying heart rate changes may not be visible to the naked eye, but the use of vital sign acquisition cameras described herein may allow detection of micro-changes in skin color.

Another vital sign measurable by vital sign acquisition cameras described herein is a patient's respiratory rate. In some embodiments, a vital sign acquisition camera may zoom in to the patient's chest and/or abdominal area to track the patient's chest or abdominal movements. The medical image device may then determine the patient's respiratory rate by detecting the patient's rate of inhalation and exhalation, which may be determined monitoring the movement of the patient's chest or diaphragm area. In some embodiments, a vital sign acquisition camera may determine whether the patient is having difficulty breathing by comparing the most-recently recorded chest movement patterns with previously-recorded chest movement patterns, e.g., stored in a patients database. Additionally or alternatively, a patient's body temperature may be determined by vital sign acquisition cameras described herein that are configured to capture thermographic or infrared images/video.

At block 124, it may be determined, e.g., by one or more components depicted in FIG. 2 (described below), based on a comparison of the updated vital sign(s) and/or physiological parameters acquired at block 122 to previously-acquired vital signs and/or physiological parameters (e.g., the initial vital signs acquired at block 110 or a previous iteration of updated vital signs/physiological parameters acquired by the vital sign acquisition cameras), whether the patient's condition has changed. For example, it may be determined whether the patient's pulse, respiratory rate, blood pressure, SO2, PPG, temperature, etc. has increased or decreased while the patient has waited. If the answer is no, then control may proceed back to block 118, and a new patient (e.g., the patient with the next highest patient acuity measure) may be identified and control may proceed back to block 120. However, if the answer at block 124 is yes (i.e. the patient's condition has changed), then control may pass to block 126. In some embodiments, the patient's condition may be represented (at least partially) by the same acuity measure used for purposes of determining monitoring order.

At block 126, it may be determined (again, by one or more components of FIG. 2) whether a medical alert is warranted based on the change detected at block 124. For example, it may be determined whether a change in one or more vital signs or patient acuity measures satisfies one or more thresholds (e.g., has blood pressure increased above a level that is considered safe for this particular patient?). If the answer is yes, then control may pass to block 128. At block 128, an alarm may be output, e.g., to a duty nurse or other medical personnel, that the patient is deteriorating. The medical personnel may then check on the patient to determine if remedial action, such as immediately admitting the patient or sending the patient to a doctor, is warranted. In some embodiments, control may then pass back to block 118. However, if the answer at block 126 is no, then in some embodiments, control may pass back to block 118.

Figure 2:
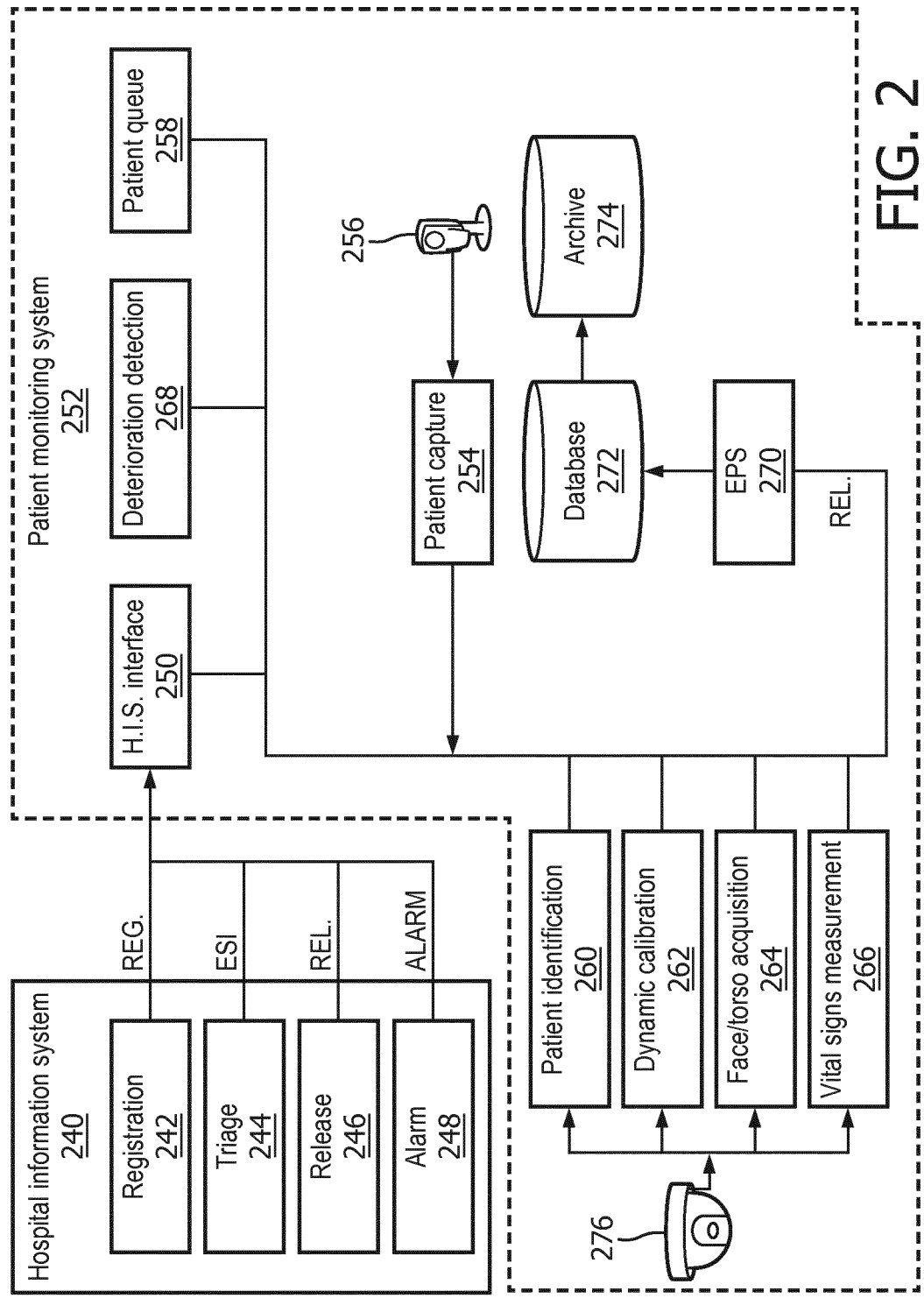
FIG. 2 illustrates an example environment in which disclosed various components may implement selected aspects of the present disclosure, in accordance with various implementations.

FIG. 2 depicts example components that may be used to practice disclosed techniques, in accordance with various embodiments. A hospital information system 240 may be of the type that is commonly found in hospitals, doctor's offices, and so forth. Hospital information system 240 may be implemented using one or more computing systems that may or may not be connected via one or more computer networks (not depicted). Hospital information system 240 may include, among other things, a registration module 242, a triage module 244, a release module 246, and an alarm module 248. One or more of modules 242-248, or any other module or engine described herein, may be implemented using any combination of hardware and software, including one or more microprocessors executing instructions stored in memory. For example, the registration module 242 may include registration instructions implementing the functionality described herein in connection with registration executing on a processor while the triage module 244 may include triage instructions implementing the functionality described herein in connection with triage executing on the same processor. Similar underlying hardware and software may be used to implement other "modules" described herein.

Registration module 242 may be configured to receive, e.g., as manual input from a duty nurse, registration information of new patients. This may include, for instance, the patient's name, age, insurance information, and so forth. Triage module 244 may be configured to receive, e.g., as manual input from a duty nurse or directly from networked medical equipment, vital signs such as those described above and/or other physiological data, such as weight, height, the patient's reason for the visit, etc. In various embodiments, vital signs received by triage module 244 and/or a patient acuity measure (e.g., ESI in FIG. 1) may be associated with corresponding patient information received by registration module 242, e.g., in one or more databases (not depicted) associated with hospital information system 240.

Alarm module 248 may be configured to receive information indicative of various events, such as patient deterioration, and raise various alarms and/or alerts in response. These alarms and/or alerts may be output using a variety of modalities, including but not limited to visual output (e.g., on display screens visible to hospital personnel), intercom announcements, text messages, emails, audio alerts, haptic alerts, pages, pop up windows, flashing lights, and so forth. Modules 242-248 of hospital information system 240 may be operably coupled, e.g., via one or computer networks (not depicted), to a hospital information system interface 250 ("H.I.S. Interface" in FIG. 2).

Hospital information system interface 250 may serve as an interface between the traditional hospital information system 240 and a patient monitoring system 252 configured with selected aspects of the present disclosure. In various embodiments, the hospital information system interface 250 may publish, e.g., to other modules of the patient monitoring system 252, various information about patients such as registration information, patient acuity measures (e.g., ESI), prescribed and/or administered medications, whether a patient has been released, various alarms/alerts, and so forth. As will be described below, in some embodiments, these publications may be provided to an event publish and subscribe ("EPS") module 270, which may then selectively store them in database 272 and/or selectively publish them to other modules of patient monitoring system 252. In some embodiments, hospital information system interface 250 may additionally or alternatively subscribe to one or more alerts or publications provided by other modules. For example, hospital information system interface 250 may subscribe alerts from deterioration detection module 268, e.g., so that hospital information system interface 250 may notify appropriate components of hospital information system 240, such as alarm module 248, that a patient is deteriorating.

Patient monitoring system 252 may include a variety of components that facilitate monitoring of patients in an area such as waiting room 104 to ensure that patients are served in a manner conducive with their actual medical condition. Patent monitoring system 252 may include, for instance, a patient capture module 254 that interfaces with one or more cameras 256, a patient queue module 258, a patient identification module 260, a dynamic calibration module 262, a face/torso acquisition module 264, a vital signs measurement module 266, a deterioration detection module 268, the aforementioned EPS module 270, and one or more databases 272, 274. As noted above, each of modules 250, 254, and 258-274 may be implemented using any combination of hardware and software. And while these modules are depicted separately, that is not meant to be limiting or to suggest each is implemented on a separate piece of hardware. For example, one or more modules may be combined and/or omitted, and one or more modules may be implemented on one or more computing systems operably connected via one or more computer networks (not depicted). The lines depicted connecting various components of FIG. 2 may represent communication channels accessible to these components. These communication channels may be implemented using any number of networking or other computer communication technologies, such as one or more buses, Ethernet, Wi-Fi, Bluetooth, Z-Wave, ZigBee, cellular communication, and so forth.

Patient monitoring system 252 may also include one or more vital sign acquisition cameras 276 that are configured to acquire, e.g., from some distance from a patient, one or more vital signs and/or physiological parameters of the patient. Examples of such vital sign acquisition cameras were described above. In various embodiments, a vital sign acquisition camera 276 may be a pan-tilt-zoom ("PTZ") camera that is operable to pan, tilt, and zoom so that different parts of an area such as waiting room 104 are contained within its field of view. In this manner, it is possible to scan the area being monitored to locate different patients, so that updated vital signs and/or physiological parameters may be acquired unobtrusively.

Patient capture module 254 may receive, from one or more cameras 256, one or more signals carrying captured image data of a patient. For example, in some embodiments, patient capture module 254 may receive a video stream from camera 256. Patient capture module 254 may perform image processing (e.g., face detection, segmentation, shape detection to detect human form, etc.) on the video stream to detect when a patient is present, and may capture a reference image of the patient in response to the detection. In some embodiments, the reference image may be captured at a higher resolution than individual frames of the video stream, although this is not required. In some embodiments, camera 256 may be a standalone camera, such as a webcam, a PTZ camera (e.g., 276), and so forth, that is deployed in or near pre-waiting room area(s) 102. The one or more images captured by camera 256 may be used thereafter as reference patient images that is associated with the patient and used later to identify the patient in the area being monitored.

Patient queue module 258 may be configured to establish and/or maintain a priority queue, e.g., in a database, of patients in the area being monitored. In various embodiments, the queue may be ordered by various parameters. In some embodiments, patients in the queue may be ranked in order of patient acuity measures (i.e. by priority). For example, the most critical patients may be placed near the front of the queue and less critical patients may be placed near the end of the queue, or vice versa. In some embodiments, updated vital signs may be acquired from patients waiting in the area being monitored, such as waiting room 104, in an order of the queue. In other embodiments, updated vital signs may be acquired from patients in a FIFO or round robin order. In other embodiments, updated vital signs may be acquired from patients in an order that corresponds to a predetermined scan trajectory programmed into vital sign acquisition camera 276 (e.g., scan each row of chairs in order).

Patient identification module 260 may be configured to use one or more signals received from vital sign acquisition camera 276, in conjunction with one or more reference patient images captured by patient capture module 254, to locate one or more patients in the area being monitored (e.g., waiting room 104). Patient identification module 260 may use various image processing techniques to identify patients using various visual features of patients. These visual features that may be used to recognize patients may include but are not limited to facial features, torso features, clothing, hair, posture, and so forth.

In some embodiments, patient identification module 260 may search an area being monitored for particular patients from which to obtain updated vital signs. For example, patient identification module 260 may search the area being monitored for a patient identified by patient queue module 258, which may be, for instance, the patient in the queue having the highest patient acuity measure. In some embodiments, patient identification module 260 may cause vital sign acquisition camera(s) 276 to scan the area being monitored (e.g., waiting room 104) until the identified patient is identified.

Dynamic calibration module 262 may be configured to track the use of vital sign acquisition camera(s) 276 and calibrate them as needed. For instance, dynamic calibration module 262 may ensure that whenever vital sign acquisition camera 276 is instructed to point to a particular PTZ location, it always points to the same place. PTZ cameras may be in constant or at least frequent motion. Accordingly, their mechanical components may be subject to wear and tear. Small mechanical errors/biases may accumulate and cause vital sign acquisition camera 276 to respond, over time, differently to a given PTZ command. Dynamic calibration module 262 may correct this, for instance, by occasionally running a calibration routine in which landmarks (e.g., indicia such as small stickers on the wall) may be used to train a correction mechanism that will make vital sign acquisition camera 276 respond appropriately Once a patient identified from patient queue 258 is recognized by patient identification module 260, face/torso acquisition module 264 may be configured to pan, tilt, and/or zoom one or more vital sign acquisition cameras 276 so that their fields of view capture a desired portion of the patient. For example, in some embodiments, face/torso acquisition module 264 may pan, tilt, or zoom a vital sign acquisition camera 276 so that it is focused on a patient's face and/or torso. Additionally or alternatively, face/torso acquisition module 264 may pan, tilt, or zoom one vital sign acquisition camera 276 to capture the patient's face, and another to capture the patient's torso. Various vital signs and/or physiological parameters may then be acquired. For instance, vital signs such as the patient's pulse, $SpO_2$, respiratory rate, and blood pressure may be obtained, e.g., by vital signs measurement module 266, by performing image processing on an image/video of the patient's face captured by vital sign acquisition camera(s) 276. Vital signs and/or physiological parameters such as the patient's respiratory rate, general posture (which may indicate pain and/or injury), and so forth may be obtained, e.g., by vital signs measurement module 266, by performing image processing on an image/video of the patient's torso captured by vital sign acquisition camera(s) 276. Of course, the face and torso are just two examples of body portions that may be examined to obtain vital signs, and are not meant to be limiting.

Deterioration detection module 268 may be configured to analyze one or more signals to determine whether a condition of a registered patient is deteriorating, improving, and/or remaining stable. In some embodiments, the patient condition may be represented, at least in part, by the same patient acuity measures described above for determining order of patients for monitoring. As such, the deterioration detection module 268 may include one or more CDS, case-based reasoning, or other clinical reasoning algorithms as described herein or other clinical reasoning algorithms (e.g., trained logistic regression models or other machine learning models) for assessing patient condition measures other than acuity measures described herein. In some embodiments, the algorithms for assessing patient acuity or other measures of patient condition employed by the deterioration detection module 268 may be updated from time to time by, for example, writing new trained weights (e.g., theta values) for a selected machine learning module or providing new instructions for execution by a processor (e.g. in the form of a java archive, JAR, file or compiled library). These signals may include, for instance, a patient's initial vital signs and other physiological information (e.g., obtained at blocks 108-110 of FIG. 1), updated vital signs obtained by vital signs measurement module 266, a patients initial patient acuity measure (e.g., calculated during registration), and/or a patient's updated patient acuity measure (e.g., calculated based on updated vital signs and/or physiological parameters received from vital signs measurement module 266). Based on determinations made using these signals, deterioration detection module 268 may send various alerts to various other modules to take various actions. For example, deterioration detection module 268 may publish an alert, e.g., by sending the alert to EPS module 270 so that EPS module can publish the alert to subscribed modules, such as alarm module 240 of hospital information system 240. In some embodiments, such an alert may include, for instance, a patient's name (or more generally, a patient identifier), a picture, the patient's last detected location in the waiting room, baseline vital signs, one or more updated vital signs, and/or an indication of a patient acuity measure. On receipt of the alert, alarm module 248 may raise an alert or alarm to medical personnel of the patient's deterioration and, among other things, the patient's last detected location in the waiting room.

EPS module 270 may be a general communication hub that is configured to distribute events released by various other components of FIG. 2. In some embodiments, all or at least some of the other modules depicted in FIG. 2 may generate events that indicate some form of result/determination/computation/decision from that module. These events may be sent, or "published," to EPS module 270. All or some of the other modules depicted in FIG. 2 may elect to receive, or "subscribe to," any event from any other module. When EPS module 270 receives an event, it may sent data indicative of the event (e.g., forward the event) to all modules that have subscribed to that event.

In some embodiments, EPS module 270 may be in communication with one or more databases, such as database 272 and/or archive 274 (which may be optional). In some embodiments, EPS module 270 may accept remote procedure calls ("RPC") from any module to provide access to information stored in one or more databases 272 and/or 274, and/or to add information (e.g., alerts) received from other modules to databases 272 and/or 274. Database 272 may store information contained in alerts, publications, or other communications sent/broadcast/transmitted by one or more other modules in FIG. 2. In some embodiments, database 272 may store, for instance, reference images associated with patients and/or their initial vital signs, updated vital signs (acquired by vital sign acquisition camera 276), and/or patient acuity measures. Optional archive 274 may in some embodiments store the same or similar information for a longer period of time.

It will be apparent that various hardware arrangements may be utilized to implement the patient monitoring system 252. For example, in some embodiments, a single device may implement the entire system 252 (e.g., a single server to operate the camera 276 to perform the vitals acquisition functions 260-266 and to perform the vitals analysis and alerting functions including deterioration detection 268 and queue management 258). In other embodiments, multiple independent devices may form the system 252. For example, a first device may drive the camera 276 and implement functions 260-266 while another server may perform the remaining functions. In some such embodiments, one device may be local to the waiting room while another may be remote (e.g., implemented as a virtual machine in a geographically distant cloud computing architecture). In some embodiments, a device (e.g., including a processor and memory) may be disposed within the camera 276 itself and, as such, the camera 276 may not simply be a dumb peripheral and, instead may perform the vital signs functions 260-266. In some such embodiments, another server may provide indications (e.g. identifiers, full records, or registered facial images) to the camera 276 to request that vitals be returned for further processing. In some such embodiments, additional functionality may be provided on-board the camera 276 such as, for example, the deterioration detection 268 (or preprocessing therefor) and/or patient queue 258 management may be performed on-board the camera 276. In some embodiments, the camera 276 may even implement the HIS interface 250 or EPS 270. Various additional arrangements will be apparent.

Figure 3:
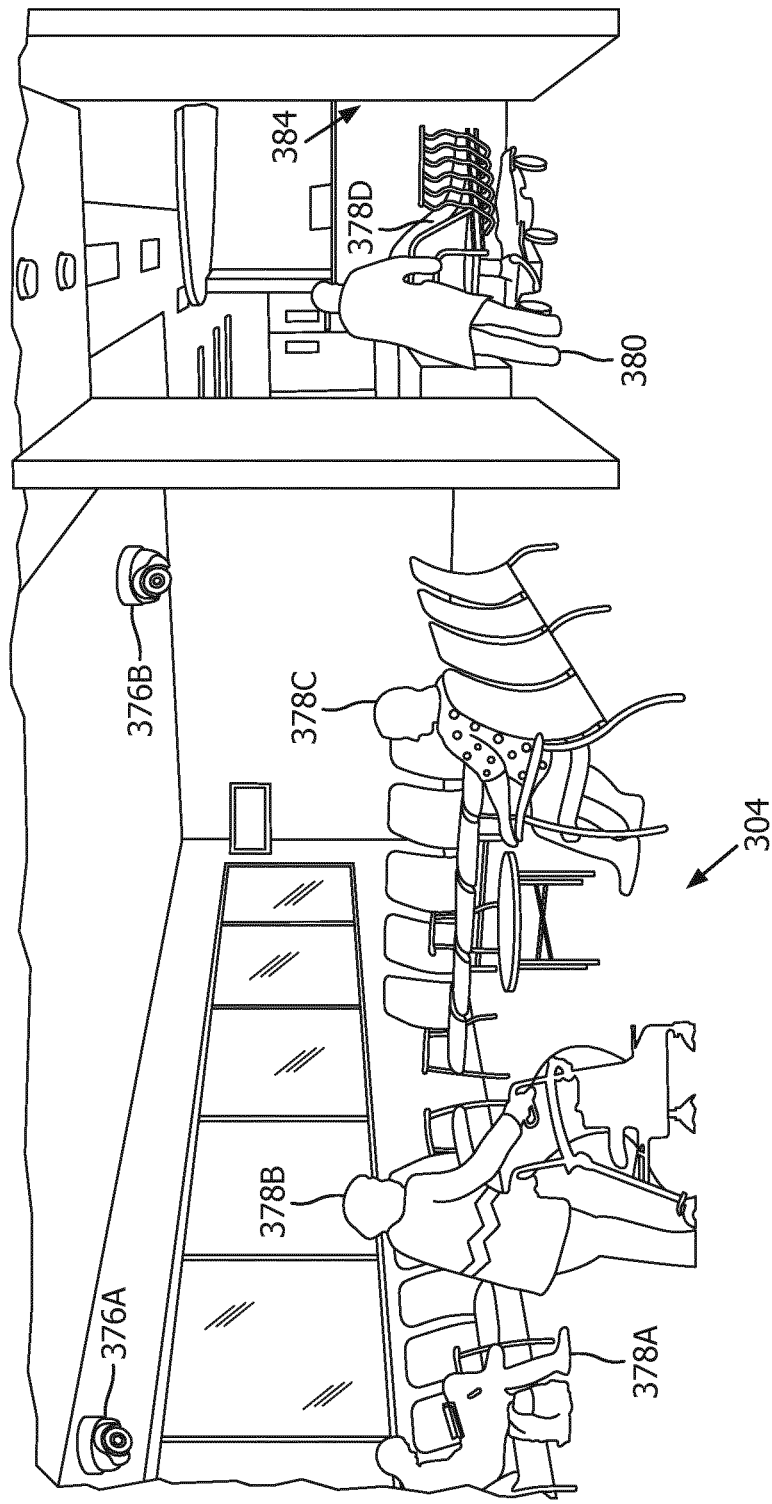
FIG. 3 and FIG. 4 each depict an example scenario in which disclosed techniques may be practiced, in accordance with various embodiments.

FIG. 3 illustrates an example scenario in which disclosed techniques may be implemented to monitor a plurality of patients 378A-C in a waiting room 304. In this example, three patients 378A-C are waiting in a hospital waiting room 304 to be attended to by medical personnel 380. Two video cameras 376A, 376B are mounted on a surface (e.g., ceiling, wall) of waiting room 304. The two video cameras 376A, 376B may be used to monitor patients 378 in waiting room 304. The patients 378A-C may each be assigned a patient acuity measure by triaging medical personnel (not depicted) based on a preliminary patient condition analysis. As the patients 378 wait for an attending physician, the two video cameras 376A, 376B may monitor patients 378 as described above to detect patient deterioration. In some embodiments, a patient acuity measure associated with a patient may be updated by medical personnel in response to detection by patient monitoring system (more specifically, deterioration detection module 268) that a patient has deteriorated. In various embodiments, when a new patient enters waiting room 304, a new round of patient monitoring and prioritization may be performed, e.g., by patient monitoring system 252. The patient queue may be automatically updated, e.g., by patient queue module 258, each time a new patient enters waiting room 304. Additionally or alternatively, medical personnel may manually update the patient queue to include a newly-arrived patient after triaging.

In some embodiments, one or more updated vital signs and/or physiological parameters of the patients 378 may be acquired using video cameras 376A, 376B to detect, for example, abnormal face color or color change such as flushing or greyish pallor. Additionally or alternatively, vital sign acquisition cameras 376 may analyze patients 378 for abnormal breathing patterns such as heavy or irregular breathing. An image or video of a patient with a very pale skin color that also depicts the patient experiencing shortness of breath may be compared to the patient's reference image, e.g., stored by hospital information system 240, to determine that the patient is experiencing a heart attack. In such a scenario, an alert may be sent immediately to medical personnel, e.g., by text message, intercom announcement, output on a display screen, etc.

Suppose that in FIG. 3, first patient 378A is a student waiting for the results of his blood and urine test, second patient 378B is waiting to receive treatment for a sports injury, while third patient 378C needs to see a doctor regarding some stomach pains. Suppose a fourth patient 378D, who was earlier waiting to see a physician for some minor breathing difficulty, was detected by video cameras 376A, 376B to exhibit some symptoms warranting emergency care. An alert such as an audio or visual alert may be raised to notify medical personnel of the deterioration of fourth patient 378D. Upon receiving the alert, emergency personnel 380 may take fourth patient 378D to the emergency room 384 where she receives the necessary treatment. Once fourth patient 378D is taken to emergency room 384, the patient queue may be updated to include only those patients 378A-C still waiting for their turn in waiting room 304.

Techniques described herein are not limited to hospital waiting rooms. There are numerous other scenarios in which techniques described herein may be implemented to achieve a variety of technical advantages. For example, disclosed techniques may also be used for security monitoring of crowds in airports, arenas, and other public places. In such scenarios, rather than monitoring patients to determine patient acuity measures, individuals may be monitored for other types of measurements, such as risk measurements.

Figure 4:
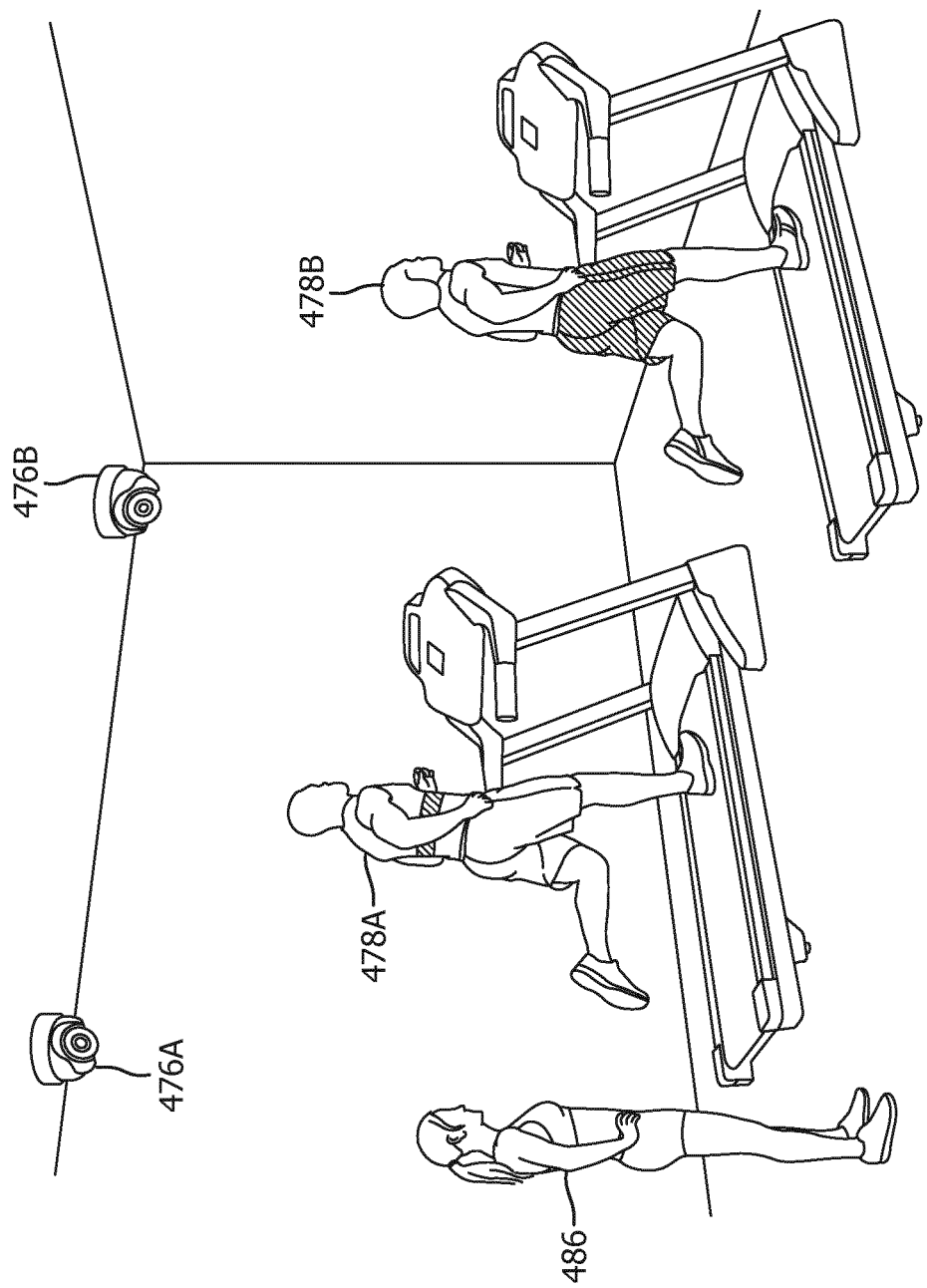

As another example, FIG. 4 depicts how disclosed techniques may be implemented in a gym. Two vital sign acquisition cameras 476A, 476B are strategically located to cover every angle required for monitoring each athlete in the gym, e.g., so that they can be used to monitor athletes 478A-B. A training instructor 486 (e.g., a coach, fitness instructor, or physical therapist) may first assess the physical condition of athletes 478 by, for example, determining whether a particular athlete feels pain during stretching due to the athlete's previous physical injury. When first athlete 478A passes the assessment, training instructor 486 may direct first athlete 478A to begin a standard training regimen. In this example, as first athlete 478A performs the assigned training regimen—for example, using the treadmill—his vital signs and/or physiological parameters such as heart rate, respiratory rate, and temperature may be continuously/ periodically monitored by vital sign acquisition cameras 476A, 476B, e.g., to determine whether first athlete 478A is over-exerting himself.

In some embodiments, at the start of the monitoring process, e.g., when first athlete 478A enters the gym to workout, one of the two vital sign acquisition cameras 476 may identify first athlete 478A, e.g., based on a reference image captured previously (e.g., when first athlete 478 joined the gym and received a photo ID). Vital sign acquisition camera 476A may zoom in to a facial area of first athlete 478A to acquire a heart rate, and then may zoom in a chest area of first athlete 478A to acquire a respiratory rate. The acquired vital signs may be transmitted by vital sign acquisition camera 476A to a computing device (not depicted, one or more components of patient monitoring system 252) for further analysis, and may be stored in a database (e.g., 272, 274). If the acquired vital signs exceed a certain threshold level, a notification (e.g., in the form of audible signal or a visual alert) may be generated to alert training instructor 486 about the exceeded threshold. In some embodiments, the computing device may recommend specific steps to be performed by first athlete 476A, such as stretching and adequate breaks between training sessions. Similar techniques may be applied to other athletes, such as second athlete 478B, depending on their respective health conditions. In some embodiments, rather than monitoring for signs of injury, techniques described herein may be used in a gym or similar setting to track calories burned or other physiological metrics, e.g., based on athlete movement, weight, temperature, pulse, respiration rate, etc., that are tracked by vital sign acquisition cameras 476 over time. To adapt the system of FIG. 2 to this setting, the deterioration detection module 268 may simply be provided with an algorithm for deriving calorie burn (or other metrics) from the available parameters. In some embodiments, the system may include a competitive component such as, for example, a display visible to people in the room showing the calories burned or other metrics of each person in the room, potentially ranked in order of highest calories burned or best other metrics observed.

Figure 5:
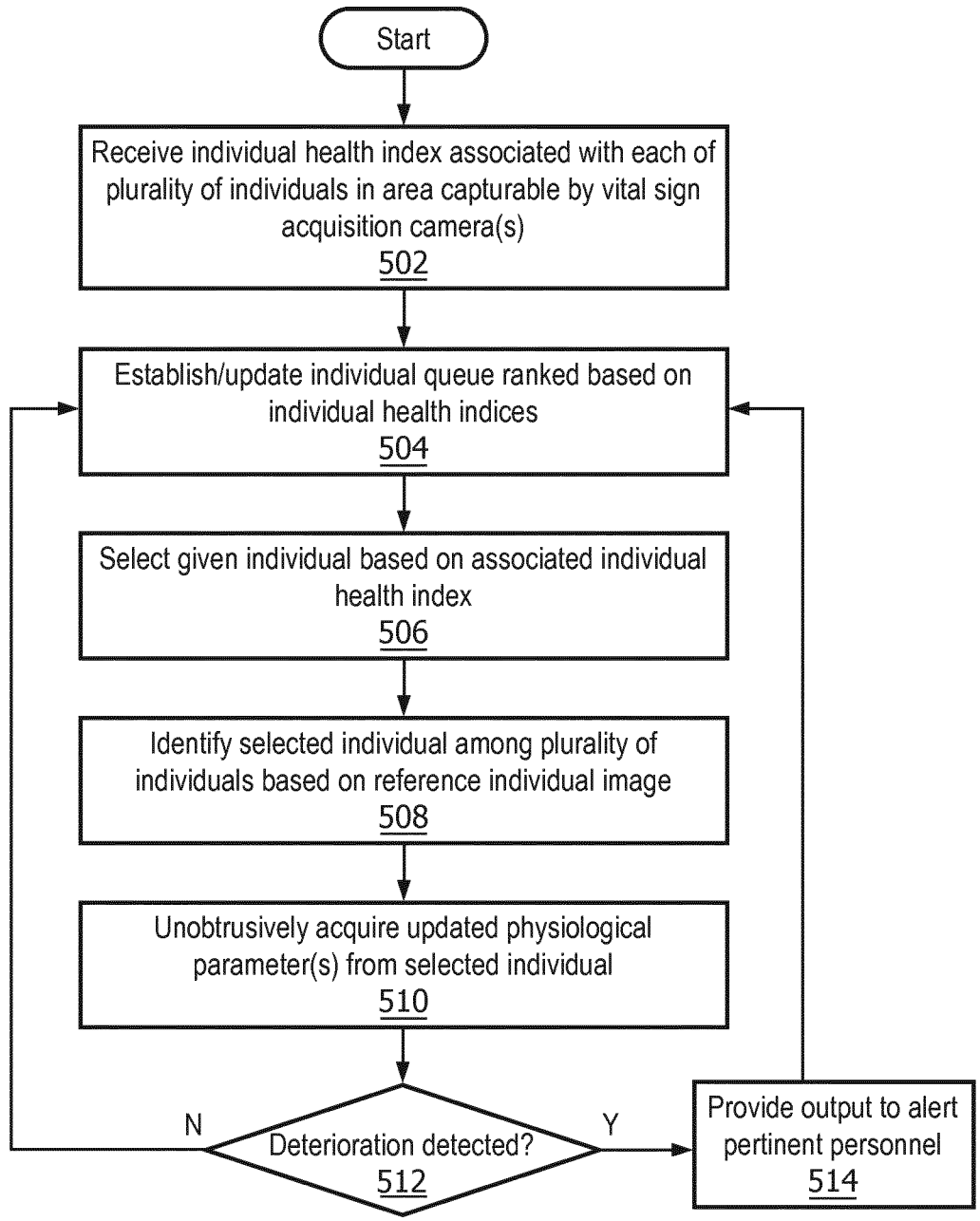
FIG. 5 depicts an example method of monitoring individuals in an area, in accordance with various embodiments.

FIG. 5 depicts an example method 500 for monitoring a plurality of individuals such as patients in an area such as a waiting room, gym, and so forth. For convenience, some of the operations of method 500 are described with reference to a system that performs the operations. This system may include various components of various computer systems. For instance, some operations may be performed by one or more components of patient monitoring system 252. Moreover, while operations of method 500 are shown in a particular order, this is not meant to be limiting. One or more operations may be reordered, omitted or added.

At block 502, individual health indices (e.g., patient acuity measure, workout intensity measure, ESI, etc.) may be received, e.g., from medical personnel (e.g., at triage), for a plurality of individuals (e.g., patients, athletes, residents of a nursing home, etc.) located in an area such as a waiting room that is capable of being captured in fields of view of the above-described vital sign acquisition cameras (which as noted above may have adjustable fields of view by virtue of panning, tilting, and/or zooming). For example, in various embodiments, prior to entering the monitored area, one or more initial vital signs and/or physiological parameters may be acquired from each individual, e.g., by a triage nurse or trainer. Based on these initial vital signs and/or physiological parameters, individual health indices may be determined, e.g., by medical personnel, for each individual in the area at block 502.

At block 504, the system may establish (or update, if it already exists) a queue (e.g., a patient queue) of individuals in the area. In various embodiments, the queue may be ordered and/or ranked based at least in part on the individual health indices determined at block 502. Additionally or alternatively, in some embodiments, the queue may be ordered based on other data points, including but not limited to the time each patient arrived, how long each patient has waited, and so forth. In some embodiments, when flow returns from block 512 or 514, block 504 may include placing the most recently monitored patient back on the queue (or otherwise placing a new entry for the patient in the queue). For example, in some embodiments, the patient may simply be placed at the end of the queue. In other embodiments, block 504 may take the patient acuity measure, deterioration measure, vitals, or other information into account such as, for example, placing the patient at a position in the queue after any patients having higher acuity measures but ahead of any patients having lower acuity measures. In other embodiments, more complex rules may be employed. For example, in some embodiments, the patient may be placed back in the queue as described but no higher than fifth (or other constant value) from the top to the queue, to help prevent the same (highest acuity) patient from being monitored repeatedly but not allowing monitoring of other patients (because they never reach the top of the queue). Alternatively, rather than a constant maximum position, the maximum position may be determined based on the current contents of the queue. For example, the maximum position may be set to equal the number (or a constant plus the number) of "high acuity" patients, identified as those patients having a patient acuity measure surpassing a preset threshold. In some embodiments, such high acuity patients may be placed at an intermediate point in the queue (according to any of the methods described herein), while others may be placed at the end of the queue. In other embodiments, the patient may be placed at a position from the front equal to the number of patients having a higher acuity measure in the queue plus one (or some other constant) to allow at least some lower acuity patients to be monitored ahead of the current patient. In some embodiments, acuity measure values (or ranges thereof) may be associated with a delay between subsequent measurements measured in, for example, number of queue positions or real time between measurements, which may then be translated into the position of the queue where the patient will be placed. In some embodiments, the patient acuity measure (or other value driving queue position placement) may take into account the time that has passed since the patient was last monitored; as such, as a patient sits in the queue, their acuity measure (or other queue position determining value) may gradually increase, making it more difficult for other patients to be placed ahead of that patient in the queue. In some such embodiments, a "queue priority value" may be utilized in the manner described above as applied to the patient acuity measure but may equal the patient acuity measure plus the time since the patient was last monitored (or some weighted sum of these two or additional values).

At block 506, the system may select a given individual from which updated vital signs and/or physiological parameters are to be acquired. For example, the system may select a patient from the front of the queue established in block 504 or may select a patient having a highest patient acuity measure (which in many embodiments may be the first patient in the queue). In other embodiments, the system may select individuals in different orders, such as using FIFO and/or round robin.

At block 508, the individual selected at block 506 may be identified in the monitored area by one or more vital sign acquisition camera 276, e.g., based on one or more reference images of the individual. As noted above, various visual features of individuals may be used for identification, including but not limited to facial features, posture, clothing, size, and so forth. At block 510, one or more vital sign acquisition camera 276 may unobtrusively acquire one or more updated vital signs and/or physiological parameters from the individual selected at block 506 and identified at block 508. In various embodiments, individuals may opt out of unobtrusive acquisition, e.g., by notifying a triage nurse or other personnel.

In some embodiments, at block 512, deterioration in the individual selected at block 506 and identified at block 508 may be detected based on the updated vital signs obtained at block 510 and at least one of an individual health index (e.g., patient acuity measure) associated with the given patient (e.g., determined at block 502) or initial vital signs (or updated vital signs acquired during a previous iteration of patient monitoring system 252) acquired from the given patient. If deterioration is detected, e.g., due to a difference between initial and updated vital signs satisfying a threshold, the method 500 may proceed to block 514. At block 514, various modalities of output, including but not limited to text messages, intercom announcements, visual output, audio output, haptic feedback, etc., may be provided to alert pertinent personnel of the difference, e.g., to notify a duty nurse of deterioration of a patient. In some embodiments, for example, medical personnel may be alerted of patient deterioration by displaying either a most-recently captured image of the deteriorating patient (e.g., so that medical personnel will know who to look for in the waiting room) or a live streaming video of the deteriorating patient in the waiting room. Regardless of whether method 500 proceeds to block 514 after block 512, method 500 may proceed back to block 504 to update the queue, e.g., to reorder the queue so that the patient having the next highest patient acuity measure may be monitored).

While examples described herein have primarily involved vital sign acquisition cameras such as cameras configured to perform contactless acquisition of vital signs and/or physiological parameters, this is not meant to be limiting. In various embodiments, other types of sensors may be incorporated into vital sign acquisition cameras and/or deployed separately to detect vital signs and/or physiological parameters of patients. For example, motion sensors may be used, for example, to detect abnormal motions of a patient in a waiting room such as those due to a patient undergoing a seizure. Various types of motion sensors may be employed, including but not limited to infrared, optical, microwave, ultrasonic, acoustic, or tomographic based sensors, as well as those that fall under the category of occupancy sensors. Motion sensors may be passive and/or dynamic. Passive infrared sensors, for instance, detect heat movement by way of a pyroelectric sensor designed to detect infrared radiation radiated by a moving body. Ultrasonic sensors, by contrast, may leverage the Doppler-shift principle. An ultrasonic sensor may transmit high frequency sound waves in a monitored area and detect reflected wave patterns. Microwave sensors may work in a similar fashion except that they may transmit high frequency microwaves rather than sound waves.

Figure 6:
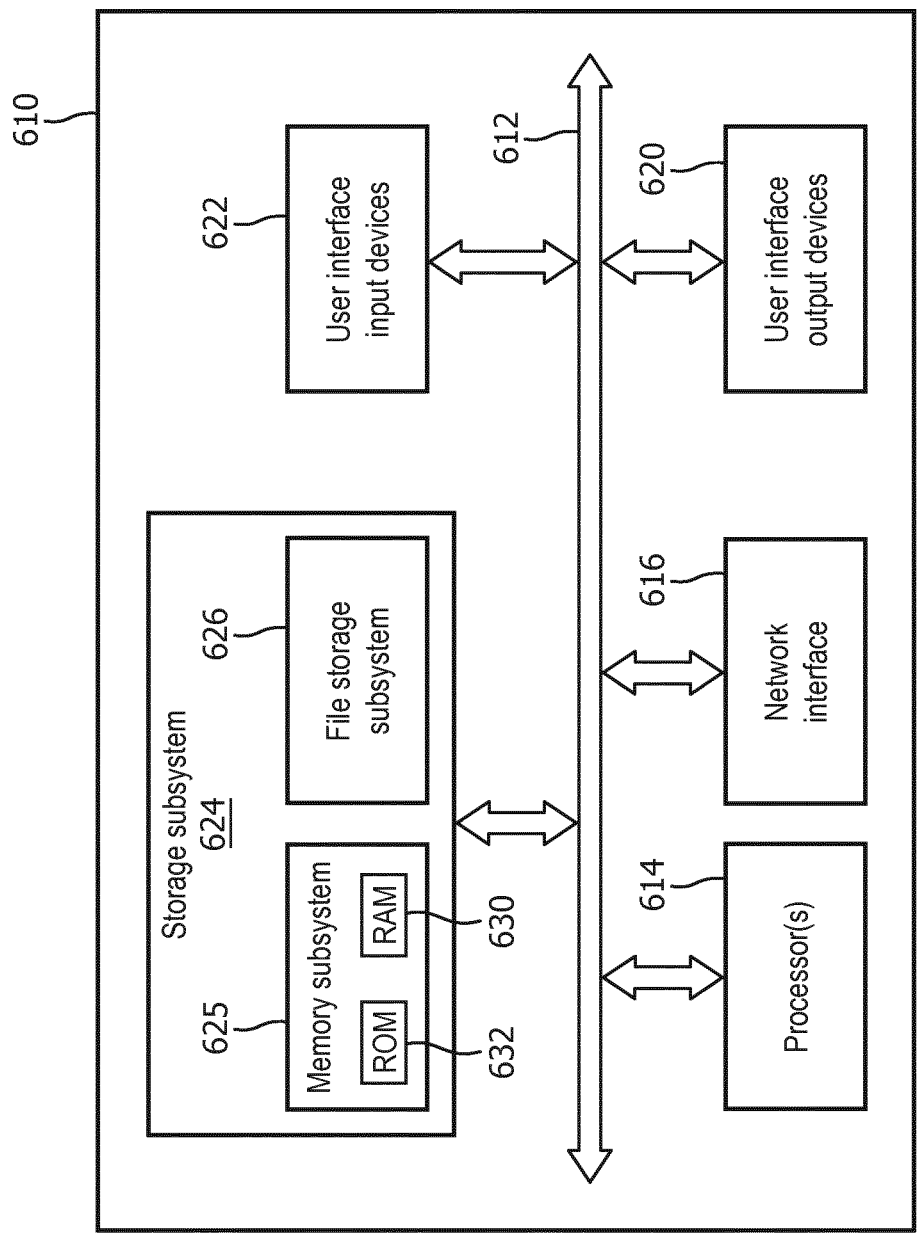
FIG. 6 depicts components of an example computer system.

FIG. 6 is a block diagram of an example computer system 610. Computer system 610 typically includes at least one processor 614 which communicates with a number of peripheral devices via bus subsystem 612. As used herein, the term "processor" will be understood to encompass various devices capable of performing the various functionalities attributed to the CDS system described herein such as, for example, microprocessors, FPGAs, ASICs, other similar devices, and combinations thereof. These peripheral devices may include a data retention subsystem 624, including, for example, a memory subsystem 625 and a file storage subsystem 626, user interface output devices 620, user interface input devices 622, and a network interface subsystem 616. The input and output devices allow user interaction with computer system 610. Network interface subsystem 616 provides an interface to outside networks and is coupled to corresponding interface devices in other computer systems.

User interface input devices 622 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 610 or onto a communication network.

User interface output devices 620 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 610 to the user or to another machine or computer system.

Data retention system 624 stores programming and data constructs that provide the functionality of some or all of the modules described herein. For example, the data retention system 624 may include the logic to perform selected aspects of method 500, and/or to implement one or more components of patient monitoring system 252.

These software modules are generally executed by processor 614 alone or in combination with other processors. Memory 625 used in the storage subsystem can include a number of memories including a main random access memory (RAM) 630 for storage of instructions and data during program execution, a read only memory (ROM) 632 in which fixed instructions are stored, and other types of memories such as instruction/data caches (which may additionally or alternatively be integral with at least one processor 614). A file storage subsystem 626 can provide persistent storage for program and data files, and may include a hard disk drive, a floppy disk drive along with associated removable media, a CD-ROM drive, an optical drive, or removable media cartridges. The modules implementing the functionality of certain implementations may be stored by file storage subsystem 626 in the data retention system 624, or in other machines accessible by the processor(s) 614. As used herein, the term "non-transitory computer-readable medium" will be understood to encompass both volatile memory (e.g. DRAM and SRAM) and non-volatile memory (e.g. flash memory, magnetic storage, and optical storage) but to exclude transitory signals.

Bus subsystem 612 provides a mechanism for letting the various components and subsystems of computer system 610 communicate with each other as intended. Although bus subsystem 612 is shown schematically as a single bus, alternative implementations of the bus subsystem may use multiple busses.

Computer system 610 can be of varying types including a workstation, server, computing cluster, blade server, server farm, or any other data processing system or computing device. In some embodiments, computer system 610 may be implemented within a cloud computing environment. Due to the ever-changing nature of computers and networks, the description of computer system 610 depicted in FIG. 6 is intended only as a specific example for purposes of illustrating some implementations. Many other configurations of computer system 610 are possible having more or fewer components than the computer system depicted in FIG. 6.

FIG. 7 shows a schematic diagram of a first embodiment of a vital sign acquisition camera 776 that may be employed in various embodiments described herein. Electromagnetic radiation 782, in particular light in the visible and infrared wavelength range, reflected from a living being 784, such as a patient, is received and evaluated by said camera 776 to generate a biometrical signal 798 of the living being 784. The camera 776 may include a filter 786 for blocking incident visible light within the incident electromagnetic radiation 782 in a wavelength range up to substantially 550 nm, and/or up to approximately 600 nm, and/or up to 650 nm. The filtered incident light 788 is then sensed by a color sensor 790 that generates at least two different color signals $792_A$, $792_B$, e.g. by use of two separate color detectors 793, 794 (or an array of such color detectors). A combination unit 795 generates at least one combined color signal 796 by combining said color signals $792_A$, $792_B$, e.g. by a linear combination. Finally, a processing unit 797 is provided for processing said combined color signal 796 and extracting at least one biometrical signal 798 of the living being 784. The combination unit 795 and the processing unit 797 may be realized in some embodiments by a common processor 799, e.g. as processing elements of a processor or implemented in software on a conventional processor. However, they may also be realized in a different manner, e.g. as dedicated hardware elements.

FIG. 8 schematically shows a second embodiment of a camera 876' that may be employed in various embodiments described herein. FIG. 8 shows that optionally an additional filter 886' may be provided (in this and/or other embodiments), which filter 886' is configured to block incident light in a wavelength range above at least 1100 nm, in particular above at least 1000 nm, before reaching the color sensor 890. While generally those color sensors, e.g. imaging silicon sensors, show a sensitivity that naturally decreases towards longer wavelengths, such an additional filter 886' may ensure that signal contributions within the filtered incident light 888 above said upper threshold wavelength are blocked, i.e. signal contributions in which water absorption becomes dominant are blocked in the twice filtered incident light 888'.

Further, in this embodiment the color sensor 890 generates three different color signals $892_A$, $892_B$, $892_C$, e.g. by use of a color filter array 893 having three different color filter areas provided in front of a photo detector 895 (or, more generally, the image sensor). Such a color sensor (e.g. including a color filter array having only two color filter areas) could also be used in the embodiment shown in FIG. 7. In some embodiments, the color sensor 890 may include a color filter array generating a red color signal $892_A$, a green color signal $892_B$ and a blue color signal $892_C$ as conventionally provided by an RGB color sensor. From the three color signals $892_A$, $892_B$, $892_C$, the combination unit 895 generates two combined color signals $896_A$, $896_B$ by making two different combinations, in particular linear combinations, of at least two of said three color signals $892_A$, $892_B$, $892_C$. From these two combined color signals $896_A$, $896_B$ the processing unit then finally extracts the desired biometrical signal 898 from the living being 884.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope

What is claimed is:

1. A computer-implemented method, comprising:
   acquiring one or more initial vital signs from each of a plurality of patients;
   determining a patient acuity measure associated with each of the plurality of patients based on the acquired one or more initial vital signs from each of the plurality of patients;
   establishing, by one or more processors, a patient monitoring queue that includes the plurality of patients, the plurality of patients being located in an area that can be captured by one or more vital sign acquisition cameras;
   unobtrusively acquiring, by one or more of the vital sign acquisition cameras, one or more updated vital signs from a given patient selected from the patient monitoring queue;
   determining, by one or more of the processors, an updated patient acuity measure for the given patient based on the one or more updated vital signs unobtrusively acquired by the one or more vital sign acquisition camera from the given patient using a machine learning model, detecting, by one or more of the processors, based on a comparison of the updated patient acuity measure for the given patient and the previously determined patient acuity measure for the given patient, deterioration of the given patient;

updating, by one or more of the processors, the machine learning model by writing new trained weights for at least one module of the machine learning model; and providing, by one or more of the processors, output alerting medical personnel of the deterioration of the given patient, wherein the one or more vital signs cameras acquire the one or more updated vital signs by applying image detection algorithms, and wherein the one or more updated vital signs comprise one or more of blood pressure, pulse, glucose level, $SO_2$, photoplethysmogram, respiration rate, temperature, skin color, blood pressure, posture, or sweat levels.

2. The computer-implemented method of claim 1, wherein the patient monitoring queue is ranked based at least in part on the patient acuity measures.

3. The computer-implemented method of claim 2, wherein the one or more initial vital signs acquired from each patient are acquired with medical equipment that is different than the one or more vital sign acquisition cameras.

4. The computer-implemented method of claim 2, wherein the given patient is selected from the patient monitoring queue based on a position of the given patient in the patient monitoring queue.

5. The computer-implemented method of claim 4, further comprising altering, by one or more of the processors, a position of the given patient in the patient monitoring queue based at least in part on the updated patient acuity measure.

6. The computer-implemented method of claim 1, further comprising identifying, by one or more of the processors, the given patient among the plurality of patients in the area based on a reference image depicting the given patient.

7. The computer-implemented method of claim 1, wherein the area comprises a medical waiting room.

8. The computer-implemented method of claim 1, wherein the one or more vital sign acquisition cameras includes a pan-tilt-zoom ("PTZ") camera.

9. A system comprising:
one or more processors;
one or more vital sign acquisition cameras operably coupled with the one or more processors; and
memory operably coupled with the one or more processors, wherein the memory stores instructions that, in response to execution of the instructions by one or more processors, cause the one or more processors to:
acquire one or more initial vital signs from each of a plurality of patients;
determine a patient acuity measure associated with each of the plurality of patients based on the acquired one or more vital signs from each of the plurality of patients;
establish a patient monitoring queue that includes the plurality of patients, the plurality of patients being located an area that can be captured by the one or more vital sign acquisition cameras;
unobtrusively acquire, by one or more of the vital sign acquisition cameras, one or more updated vital signs from a given patient selected from the patient monitoring queue;
determine an updated patient acuity measure for the given patient based on the one or more updated vital signs unobtrusively acquired by the one or more vital sign acquisition cameras from the given patient using a machine learning model;
detect, based on a comparison of the updated patient acuity measure for the given patient and the previously determined patient acuity measure for the given patient, deterioration of the given patient;
update the machine learning model by writing new trained weights for a least one module of the machine learning model; and
provide output alerting medical personnel of the deterioration of the given patient,
wherein the one or more vital signs cameras acquire the one or more updated vital signs by applying image detection algorithms, and
wherein the one or more updated vital signs comprise one or more of blood pressure, pulse, glucose level, $SO_2$, photoplethysmogram, respiration rate, temperature, skin color, blood pressure, posture, or sweat levels.

10. The system of claim 9, wherein the plurality of patients are ranked in the patient monitoring queue based at least in part on the patient acuity measures.

11. The system of claim 9, wherein the given patient is selected from the patient monitoring queue based on a position of the given patient in the patient monitoring queue.

12. The system of claim 9, wherein the output comprises one or both of a reference image of the given patient and a location of the given patient in the area.

13. The system of claim 10, further comprising altering, by one or more of the processors, a position of the given patient in the patient monitoring queue based at least in part on the updated patient acuity measure.

14. The system of claim 9, further comprising identifying, by one or more of the processors, the given patient among the plurality of patients in the area based on a reference image depicting the given patient.

15. At least one non-transitory computer-readable medium comprising instructions that, in response to execution of the instructions by one or more processors, cause the one or more processors to perform the following operations:
acquiring one or more initial vital signs from each of a plurality of patients;
determining a patient acuity measure associated with each of the plurality of patients based on the acquired one or more initial vital signs from each of the plurality of patients;
establishing a patient monitoring queue that includes the plurality of patients, the plurality of patient being located in an area that can be captured by one or more vital sign acquisition cameras;
unobtrusively acquiring, by one or more of the vital sign acquisition cameras, one or more updated vital signs from a given patient selected from the patient monitoring queue;
determining an updated patient acuity measure for the given patient based on the one or more updated vital signs unobtrusively acquired by the one or more vital sign acquisition cameras from the given patient using a machine learning model;
detecting, based on a comparison of the updated patient acuity measure for the given patient and the previously determined patient acuity measure for the given patient, deterioration of the given patient;
updating the machine learning model by writing new trained weights for at least one module of the machine learning model; and providing output alerting medical personnel of the deterioration of the given patient, wherein the one or more vital signs cameras acquire the one or more updated vital signs by applying image detection algorithms, and wherein the one or more updated vital signs comprise one or more of blood pressure, pulse, glucose level, $SO_2$, photoplethysmogram, respiration rate, temperature, skin color, blood pressure, posture, or sweat levels.

* * * * *